United States Patent [19]

Liboff et al.

[11] Patent Number: 5,088,976
[45] Date of Patent: * Feb. 18, 1992

[54] DEFORMABLE MAGNETIC FIELD AIDING COILS FOR USE IN CONTROLLING TISSUE GROWTH

[75] Inventor: Abraham R. Liboff, Birmingham, Mich.; Stephen D. Smith, Lexington, Ky.; Bruce R. McLeod, Bozeman, Mo.

[73] Assignee: Life Resonances, Inc., Bozeman, Mo.

[*] Notice: The portion of the term of this patent subsequent to Jun. 12, 2007 has been disclaimed.

[21] Appl. No.: 280,395

[22] Filed: Dec. 5, 1988

Related U.S. Application Data

[63] Continuation-in-part of Ser. No. 172,268, Mar. 23, 1988, Pat. No. 4,932,951.

[51] Int. Cl.$^5$ ............................................ A61N 2/04
[52] U.S. Cl. ....................................... 600/13; 600/15; 602/2
[58] Field of Search ............................ 600/13, 14, 15; 128/419 F, 82.1

[56] References Cited

U.S. PATENT DOCUMENTS

| | | |
|---|---|---|
| 4,266,532 | 5/1981 | Ryaby et al. |
| 4,456,001 | 6/1984 | Pescatore. |
| 4,501,265 | 2/1985 | Pescatore. |
| 4,548,208 | 10/1985 | Niemi ........................ 128/419 F |
| 4,550,714 | 11/1985 | Talish et al. ................... 600/15 |
| 4,561,426 | 12/1985 | Stewart. |
| 4,616,629 | 10/1986 | Moore. |
| 4,635,643 | 1/1987 | Brown. |
| 4,932,951 | 6/1990 | Luboff et al. ................... 600/13 |

OTHER PUBLICATIONS

Liboff, Cyclotran Resonance in Membrane Transport, From: Interactions Between Electromagnetic Fields and Cells, Ed. Chianbrera et al., Plenum Publishing, 1985, pp. 281–296.

Blackman et al., Bioelectromagnetics, vol. 6, 1985, pp. 327–337.

Primary Examiner—William E. Kamm
Assistant Examiner—John Hanley
Attorney, Agent, or Firm—Dykema Gossett

[57] ABSTRACT

An apparatus and method for regulating the growth of living tissue are provided. The apparatus includes a deformable magnetic field generator and a magnetic field detector for producing a controlled, fluctuating, directionally oriented magnetic field parallel to a predetermined axis projecting through the target tissue. The deformable magnetic field generator includes a pair of field coils embedded in a flexible material which allows the field coils to be plastically deformed to fit the contour of a body region such as a patient's limb. The field detector samples the magnetic flux density along the predetermined access and provides a signal to a microprocessor which determines the average value of the flux density. The applied magnetic field is oscillated at predetermined frequencies to maintain a preselected ratio of frequency to average flux density. This ratio is maintained by adjusting the frequency of the fluctuating magnetic field and/or by adjusting the intensity of the applied magnetic field as the composite magnetic flux density changes in response to changes in the local magnetic field to which the target tissue is subjected. By maintaining these precise determined ratios of frequency to average magnetic flux density, growth characteristics of the target tissue are controlled.

10 Claims, 2 Drawing Sheets

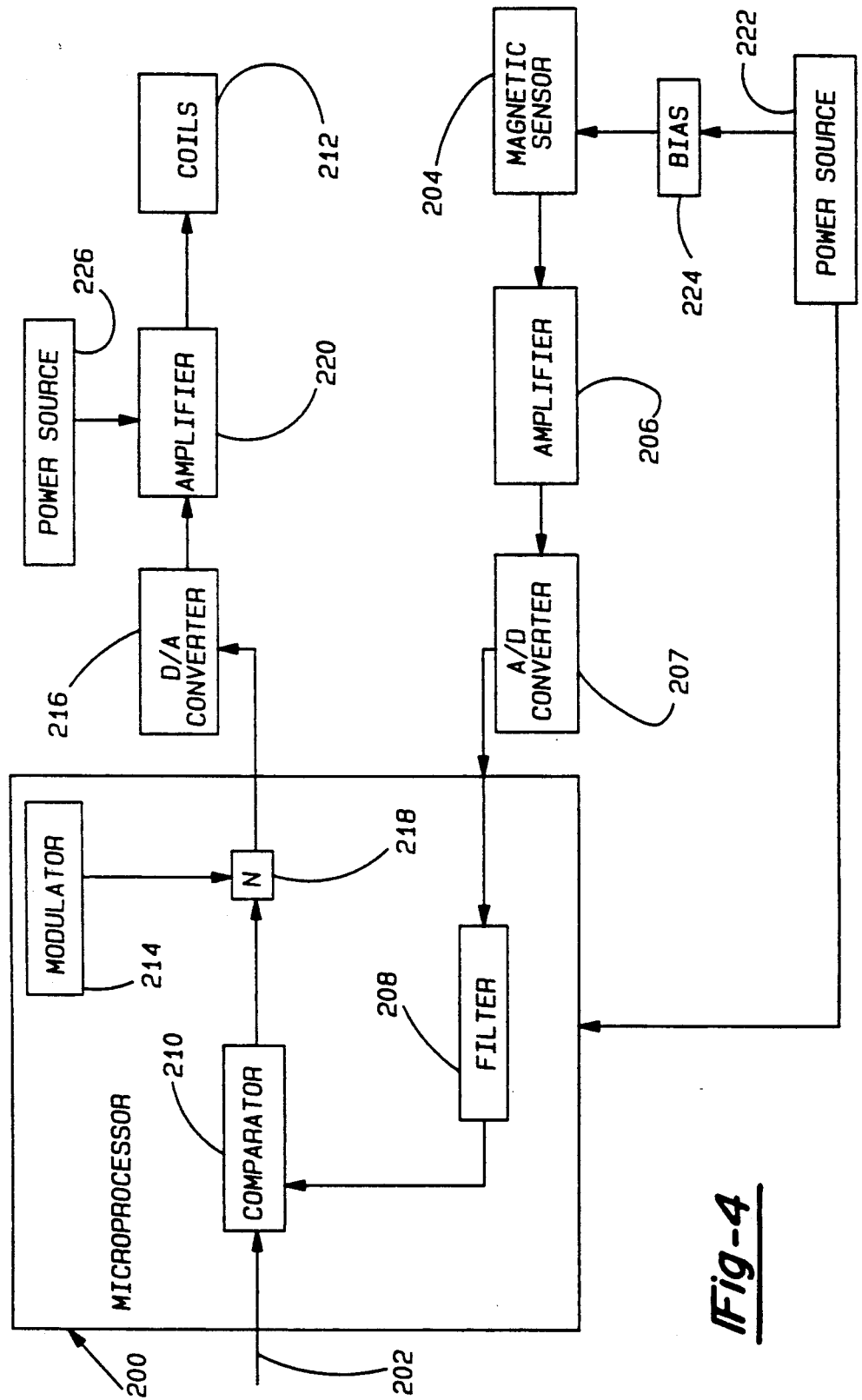

DEFORMABLE MAGNETIC FIELD AIDING COILS FOR USE IN CONTROLLING TISSUE GROWTH

This application is a continuation-in-part of U.S. patent application Ser. No. 172,268, filed Mar. 23, 1988, now U.S. Pat. No. 4,932,951 entitled "Method and Apparatus for Controlling Tissue Growth with An Applied Fluctuating Magnetic Field", which is expressly incorporated herein by reference. Also, United States Patent application entitled "Improved Method and Apparatus for Regulating Transmembrane Ion Movement", filed by the inventors of this application Ser. No. 278,688 filed Dec. 1, 1988 is expressly incorporated herein by reference.

FIELD OF THE INVENTION

The present invention relates generally to devices for generating magnetic fields for therapeutic purposes. More specifically, the present invention relates to an apparatus which includes two coils which can be conformed to the anatomical contour of a living subject such as a human. The apparatus includes means for regulating a magnetic field in a predetermined space, the predetermined space being occupied by a target tissue to be treated by the therapeutic magnetic field, which gives precise and automatic control of the magnetic field regulation.

BACKGROUND OF THE INVENTION

The inventors of the present invention devised a method and apparatus for regulating the transport of a preselected ion across a cell membrane utilizing an applied, oscillating magnetic field. This remarkable achievement is disclosed in U.S. patent application Ser. No. 923,760, now U.S. Pat. No. 4,818,697 entitled, "Techniques for Enhancing the Permeability of Ions", which was filed on Oct. 27, 1986, and the disclosure of which is incorporated herein by reference. Therein, a method and apparatus are disclosed by which transmembrane movement of a preselected ion is magnetically regulated using a time-varying magnetic field tuned to the cyclotron resonance energy absorption frequency of the preselected ion. This important discovery brought to light the interplay of local magnetic fields and the frequency dependence of ion transport mechanisms.

Having established a method by which selective ion transport can be regulated, the present inventors discovered that certain characteristics of living tissue could be controlled by application of an oscillating magnetic field having a non-zero average value. Significantly, it was determined that selected ratios of the frequency of the applied field to the flux density of the total magnetic field passing through the tissue along a predetermined axis were capable of stimulating the growth and development of the target tissue. This was demonstrated to be effective in promoting the growth of bone tissue. As a result, U.S. patent application Ser. No. 172,268, entitled "Method and Apparatus for Controlling Tissue Growth with an Applied Fluctuating Magnetic Field" was filed on Mar. 23, 1988, the disclosure of which is incorporated herein by reference.

Therein, there is provided an apparatus for controlling the growth of living tissue. The apparatus includes magnetic field generating means such as a field coil for generating a controlled, fluctuating magnetic field which penetrates a tissue, and an associated magnetic field sensing device for measuring the intensity of the magnetic field present in the tissue. In one embodiment, the magnetic field generating means and magnetic field sensor are enclosed within a housing along with a power source.

The work with tissue growth control was extended and it was discovered that tissue development can be regulated to control the growth characteristics of non-osseous, non-cartilaginous connective tissue proper and cartilaginous tissue. These inventions are disclosed, respectively, in U.S. patent application Ser. No. 254,438, entitled "Method and Apparatus for Controlling the Growth of Non-Osseous, Non-Cartilaginous Solid Connective Tissue", which was filed Oct. 6, 1988, the disclosure of which is incorporated by reference, and in U.S. patent application Ser. No. 265,265, entitled "Method and Apparatus for Controlling the Growth of Cartilage", which was filed Oct. 31, 1988, the disclosure of which is incorporated by reference.

This work further resulted in an apparatus which utilizes a feedback system to provide automatic control of the magnetic field in any application of cyclotron resonance transmembrane ion regulation. This invention is disclosed in U.S. patent application Ser. No. 278,688, filed Dec. 1, 1988, entitled "Improved Method and Apparatus for Regulating Transmembrane Ion Movement" by the inventors of this application, now U.S. Pat. No. 5,059,298. This disclosure has been incorporated by reference.

In U.S. Pat. No. 4,616,629, to Moore, a single-coil configuration adapted for embedment in an orthopedic cast for use in applying electromagnetic signals for osteogenic therapy is provided. Therein, an otherwise flat circular multiple turn coil is permanently deformed and is preferably embedded within a cast. The disclosure does not include the use of a Helmholtz configuration of a coil pair to create a uniform magnetic field within a predetermined space. The Moore disclosure does not recognize any need to determine the local magnetic field component nor is any means for measuring and automatically compensating for fluctuations in the local field provided.

It will be recognized by those skilled in the art that an idealized magnetic field occupying the space between two coils in Helmholtz configuration can be easily predicted where the coils are flat and circular. However, as the coils deviate from this geometry calculation of an applied field becomes more difficult.

It will also be appreciated that the application of a therapeutic magnetic field to a region of body tissue of either man or animal generally requires that the patient remain ambulatory to the extent possible. Thus, it is highly desirable to have an apparatus such as that disclosed by the present inventors in prior applications which can be attached to a patient and which does not substantially restrict patient movement. It would also be desirable to provide such an apparatus in which the coils that make up the Helmholtz coil pair could be adapted to conform to differences in the shape of the site of application i.e. leg, arm, or the like, and which could be reused on a number of patients having different morphological characteristics. The present invention meets these goals.

In accordance with the present invention, there is provided a deformable tissue growth stimulator which includes a pair of field coils which can be deformed to fit a range of sizes and shapes of patients and body regions. In one aspect, each coil is encased or embedded in a plastically deformable medium to form twin deformable coil pads. The pads are interconnected by a flexible belt which is provided with means for attaching the belt around a region of living tissue to be treated such as a patient's leg. In use, the treatment pads are simply bent with one's hand or the like to match the contour of the patient's body, such as a patient's arm or leg. The nature of the material in which the coils are embedded allows this plastic deformation without any resilient recoil. Once the treatment pads have been deformed in this manner, the belt is secured in position on the subject limb and treatment is administered. As will be explained more fully, the precise ratio of frequency to average magnitude of a composite magnetic field which permeates the target tissue is maintained in a manner which automatically corrects for deviations in the local magnetic field to which the tissue is subjected.

SUMMARY OF THE INVENTION

In one aspect, the present invention provides an apparatus for controlling the growth of living tissue which can be adapted to fit a variety of anatomical sites of differing geometries. The novel apparatus includes a deformable magnetic field generating means such as a pair of field coils each embedded in a plastically deformable pad for generating a controlled, fluctuating magnetic field which penetrates living tissue in man and animals and an associated magnetic field sensing device for measuring the intensity of the magnetic field present in the tissue. In a preferred embodiment, the deformable field coils are encased or embedded in a plastically deformable pad formed of non-magnetic material. A magnetic field sensor is also embedded in one of the plastically deformable pads along with a power source such as a battery or the like. In operation, the deformable coils of the magnetic field generating means are manually deformed or shaped to approximate the contour of the body region to which they will be applied. The deformable coils are then placed in position in opposed relation on the target body region such as a human limb having a fractured femur. A fluctuating, directional magnetic field is then generated by the magnetic field generating means. The applied magnetic flux density is directed along a predetermined axis which passes through the tissue to be affected. In one embodiment, the applied magnetic flux density along the axis is superimposed on that component of the local or ambient magnetic field which is parallel to the predetermined axis to create a fluctuating composite field. The resultant combined magnetic flux density which is parallel to the predetermined axis and which passes through the tissue to be affected is measured by the magnetic field sensor. The magnetic field sensor determines the net average value of the magnetic flux density which passes through the targeted tissue along the predetermined axis. In one embodiment, the frequency of the fluctuating magnetic field is set at a predetermined value and the net average value of the magnetic flux density is then regulated by adjusting the magnitude of the applied magnetic field to produce a combined magnetic field having a preselected ratio of frequency-to-field magnitude which affects the growth characteristics of the target tissue. In a preferred embodiment, changes in the magnitude of the local magnetic field along the predetermined axis which would otherwise alter the magnetic flux density of the combined magnetic field parallel to the predetermined axis and which would thus produce a deviation from the desired ratio are counterbalanced by adjustment of the magnitude of the applied, fluctuating magnetic field. This adjustment is preferably made by microprocessing means in association with both the magnetic field generating means and the magnetic field sensor. Preferred ratios of frequency-to-field magnitude are determined with reference to the equation:

$$f_c/B = q/(2\pi m)$$

where $f_c$ is the frequency of the combined magnetic field in Hertz, B is the non-zero average value of the magnetic flux density of the combined magnetic field parallel to the axis in Tesla, q/m is in Coulombs per kilogram and has a value of from about $5 \times 10^5$ to about $100 \times 10^6$. B preferably has a value not in excess of about $5 \times 10^{-4}$ Tesla. In one embodiment, the values of q and m are selected with reference to the charge and mass of a preselected ion.

In another embodiment, changes in the ambient magnetic field which would otherwise alter the ratio of frequency-to-magnetic field are counterbalanced by adjusting the frequency of the applied magnetic field to maintain the preferred ratio. The present invention also contemplates the adjustment of both frequency and field magnitude to maintain the predetermined preferred ratio. Preferably, the peak-to-peak amplitude of the AC component is in the range of about $2.0 \times 10^{-7}$ to about $2.0 \times 10^{-4}$ Tesla. The waveform is preferably substantially sinusoidal, but other waveforms are suitable.

BRIEF DESCRIPTION OF THE DRAWINGS

FIG. 4 is a block diagram of an embodiment of the present invention in which the circuit of the inventive apparatus is arbitrarily divided into convenient functional sections.

DETAILED DESCRIPTION OF THE PREFERRED EMBODIMENTS

Figure 1:
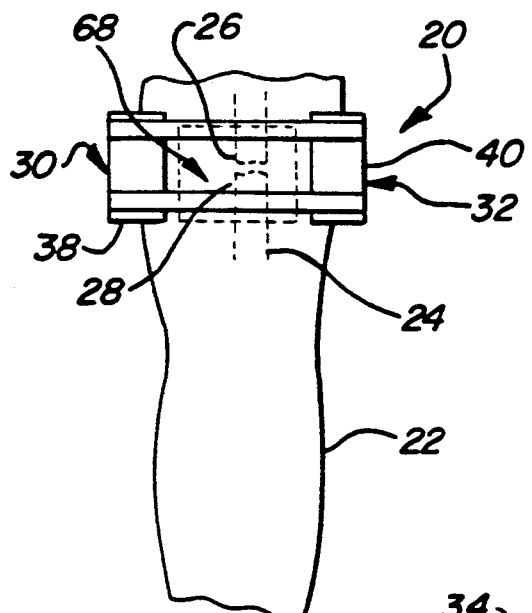
FIG. 1 is a front elevational view of the present invention as applied to the treatment of a fractured femur.

Referring now to FIG. 1 of the drawings, deformable tissue growth regulator 120 is shown in position on leg 122 of a human subject. It is to be understood that both the apparatus and the method of the present invention are suitable for use in controlling tissue growth in an animal subject or a human subject. Thus, the target tissue which is to be controlled is a region of living tissue in a subject, in other words, an "in vivo" target tissue. As used herein, the term "living tissue" shall be defined, without limiting its customary meaning, as living tissue which is capable of conducting metabolic functions such as cellular respiration and which possesses viable growth characteristics. "Growth characteristics" shall be defined, without limiting its customary meaning, as those attributes of living tissue which serve to mediate replication, growth, maintenance and repair. Although the stimulation of tissue growth will be emphasized in this description of preferred embodiments of the present invention, it is to be understood that the present invention can also be used to retard or impede the development of living tissue and may be suitable for other applications, including the prevention of abnormal tissue development.

Fractured femur 124 is shown having ends 126 and 128 which are to be stimulated by the present invention to enhance the rate at which union of the ends occurs. As will be appreciated by those skilled in the art, the natural developmental processes by which ends 126 and 128 reunite may be interrupted by a factor of known or unknown etiology resulting in delayed healing. In this embodiment, deformable tissue growth regulator 120 includes two deformable treatment pads 130 and 132 which are positioned on leg 122 in the region of ends 126 and 128 in the opposed fashion illustrated in FIG. 1. As will be explained more fully, it is important that deformable treatment pads 130 and 132 be placed adjacent the target connective tissue proper such that the tissue is within the range of the magnetic flux generated by the treatment pads. Also, although it is preferred that two treatment pads be employed in an opposed fashion as illustrated in FIG. 1, a plurality of deformable treatment pads greater than two may be suitable in some applications.

Figure 2:
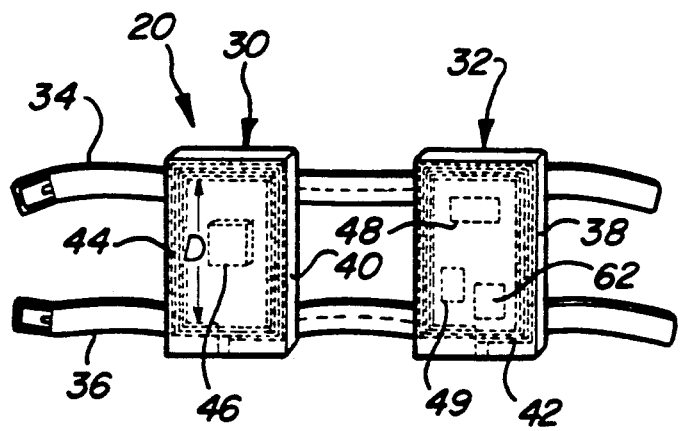
FIG. 2 is a front elevational view of the present invention with two deformable treatment pads having deformable field coils and magnetic field sensing means shown in phantom.

Referring now to FIG. 2 of the drawings, retaining straps 134 and 136 are seen by which deformable tissue growth regulator 120 is preferably secured into position on leg 122. Other securing means may be suitable or desirable in a particular application. Straps or belts 134 and 136 are attached to deformable treatment pads 130, 132 by any convenient means in a manner which allows the distance between deformable treatment pads 130, 132 to be adjusted to attain the substantially opposed orientation shown in FIG. 1. Hence, straps 130, 132 also facilitate adjustment so that deformable tissue growth regulator 120 can be used on limbs of various sizes. Treatment pads 130 and 132 should be snugly but comfortably in position to prevent substantial movement relative to the target tissue, illustrated here as fractured femur ends 126 and 128.

Figure 3:
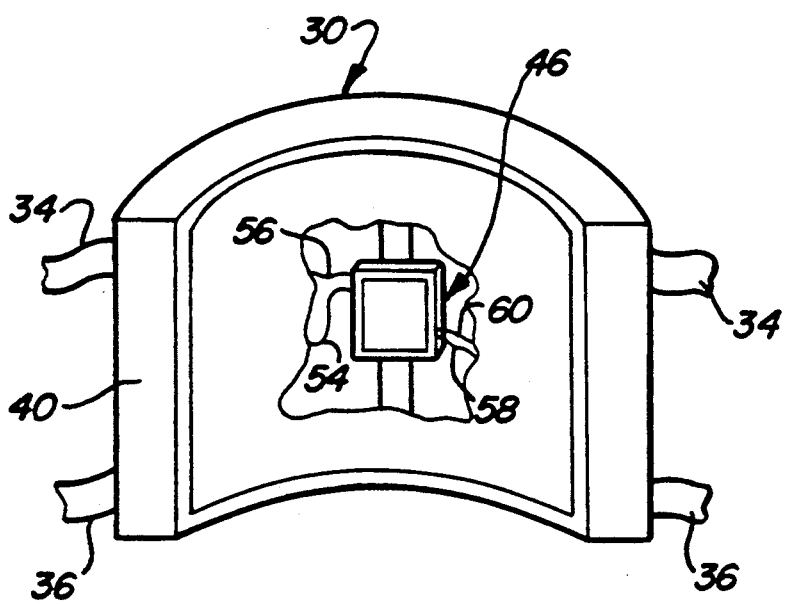
FIG. 3 is a front elevational view of one deformable treatment pad of the present invention with the pad broken away to illustrate the magnetic field sensing means.

Referring now to FIGS. 2 and 3, each deformable treatment pad 130, 132 preferably includes a support matrix or structure 138, 140 of a non-magnetic material which can be plastically deformed by manual manipulation such as by one's hands or the like. Each field coil 142, 144 is embedded in the deformable support structure 138, 140. Although in FIG. 3 support structure 140 appears hollow for purposes of illustration, each support structure is preferably solid. Field coils 142 and 144 can be partially encased or fully encased in the support matrix as shown in FIGS. 2 and 3. A number of materials are suitable for use in forming each support structure 138, 140 such as latex or another pliable material. As will be appreciated by those skilled in the art, the field coils are typically formed of a predetermined number of turns of copper wire which is quite ductile. Hence, the material used to form support structures 138 and 140 can comprise a material which yields easily as the field coil metal is deformed to a desired shape, but which is not overly resilient; that is, it does not rebound to change the configuration of the deformed field coils. A shape-retaining material can also be used which has a clay-like consistency. In other words, a material can be used which is moldable in a given shape at room temperature and which can be remolded numerous times. Although not necessarily preferred, clay could be used to form the support structures 138 and 140.

At least one deformable treatment pads includes a magnetic field sensing device 146, such as a Hall-effect device, shown in support structure 140 of deformable treatment head 130. Sensing device 146 can be completely embedded in support matrix 140. Power source 148 is provided, preferably enclosed within one of the deformable treatment pads. Power source 148 may comprise a dry cell battery or the like. It is preferred that two or more separate power sources be provided to minimize the number of circuit elements required. While it is a significant feature and advantage of the present invention to provide a deformable tissue growth regulator which includes a self-contained power source, and thus which is both lightweight and mobile, other power sources such as an ac line source may be used in connection with an ac/dc converter where mobility is not required.

As stated, field coils 144 and 142 are the preferred means by which an applied magnetic field is generated in the present invention. The radius of each field coil 144 and 142, as well as the turns of winding, may vary in accordance with the principles of the present invention. Those skilled in the art will appreciate that plastically deformable electromagnets or possibly permanent magnets may be adapted for use in the present invention and any such use is intended to come within the scope of the present invention. Field coils 144 and 142 are most preferred since they may be formed of ductile metals and they provide a simple means for concentrating magnetic lines of force. Also, the present invention includes several components within a single pad, and therefore shielding may be employed to prevent undesired interactions between components.

In the most preferred arrangement, the geometry and relative position of field coils 144, 142 during treatment are such that they approximate the magnetic field generated by a pair of Helmholtz coils. In most instances, true Helmholtz coils are considered to be flat, a geometry which does not lend itself well to the morphology of the human anatomy. Those skilled in the art will thus appreciate that in the most preferred arrangement, field coils 144, 142 are substantially identical, field-aiding, parallel coaxial coils separated by a distance equal to the radius of each coil, but curved somewhat to more closely conform to the region of the body to which they are applied. By constructing the coils in accordance with the present invention, this arrangement is made possible. In this most preferred embodiment, the configuration of the field coils produces an applied magnetic field in a predetermined space between the coils. Since the field so generated is not a idealized field of true Helmholtz coils, that is, the field may not be truly uniform in the predetermined space, it is important to monitor the resultant field which permeates the tissue being treated. This is accomplished in the present invention by magnetic field sensor 146.

It will be appreciated that the target tissue will be subject to local magnetic influences. As used herein, "local magnetic field" shall be defined as the magnetic influences, including the earth's magnetic field or geomagnetic field, which create a local magnetic flux that flows through the target tissue. "Magnetic flux density" shall be defined in the customary manner as the number of magnetic field lines per unit area of a section perpendicular to the direction of flux. Factors contributing to the local magnetic field in addition to the geomagnetic field may include localized regions of ferromagnetic materials or the like. In one embodiment of the present invention, field coils 142 and 144 are used to create an applied, fluctuating magnetic field which when combined with the local magnetic field parallel to a predetermined axis extending through the target tissue produces a resultant or combined magnetic field having a precisely controlled, predetermined ratio of magnetic flux density to frequency.

Referring now to FIG. 3 of the drawings, magnetic field sensing device or magnetometer 146 is shown in pad 140 with the appropriate leads 154, 156, 158 and 160, by which the field-sensing device is electrically connected to power source 148 and in one embodiment to microprocessing means 162. The direction of the applied magnetic flux defines the direction of predetermined axis A shown in FIG. 1. That is, the flux of the applied magnetic field is always in the same direction as predetermined axis A. In the preferred embodiment of the invention, this applied magnetic flux is superimposed on the local magnetic flux in predetermined space 168.

Magnetometer 146 is positioned in deformable tissue growth regulator 120 to measure the total or composite magnetic flux which passes through predetermined space 168 parallel to predetermined axis A. It will be understood, then, that magnetometer 146 is provided to measure the composite magnetic field along axis A. The local field component either augments or decreases the applied magnetic flux unless the local field component is zero. This is an important feature of the present invention. The relatively low applied flux densities and precise predetermined relationships of combined flux density and frequency provided by the present invention must be maintained during treatment, notwithstanding the influence of the local magnetic field. This is achieved in essentially two preferred manners which will be explained more fully herein. Thus, magnetometer 146 is provided to determine the magnitude of the magnetic flux density of the local magnetic field and measures the magnitude of the applied field which may vary somewhat depending on the degree that the field coils are deformed to match the contour of the body region to which they are fitted. Hence, in one embodiment of the invention, predetermined space 168 is occupied by a region of living tissue of a human or animal subject. Predetermined axis A which projects through predetermined space 168 and thus through the target tissue is defined by the relative position of deformable tissue growth regulator 120 with respect to the target tissue. Predetermined axis A is in the same direction as the applied magnetic flux generated by field coils 142, 144 through predetermined space 168. During this procedure, magnetometer 146 measures the total magnetic flux density parallel to predetermined axis A which passes through the target tissue. This total or composite magnetic flux density is the sum of the applied component and the local component. The local component may at times be in the same direction as the applied flux and at other times be in directions other than the applied flux. At times the local component may also be zero. These changes in the local component along the axis are produced by changes in the direction of predetermined axis A as deformable tissue growth regulator 120 is repositioned such as when an ambulatory patient receiving treatment moves leg 122. The net average value of magnetic flux density is accordingly regulated to adjust to the change in composite flux. Therefore, deformable tissue growth regulator 120 is preferably a mobile unit which is a significant advantage.

In the present invention, a fluctuating combined or composite magnetic field is created having a magnetic flux density parallel to predetermined axis A, where the combined magnetic flux density along axis A is maintained at a predetermined relationship to the frequency of the fluctuations. In this embodiment, the combined magnetic flux density parallel to predetermined axis A has a non-zero net average value. The therapeutic magnetic field of the present invention can be thought of as a static field having reference level on which a fluctuating magnetic field is superimposed. It comprises an ac component which varies in amplitude but not direction and a dc reference around which the ac component varies. Therefore, the reference level is the non-zero average value of the flux density (B). Therefore, it will be understood that the non-zero average or net average value of the composite magnetic flux density along predetermined axis A is utilized since the magnitude B of the composite flux density changes at a predetermined rate due to oscillation or fluctuation of the applied magnetic flux. Thus, an average value is utilized which is a non-zero average value. This reflects that although the composite magnetic flux density along the axis is oscillating at a controlled rate, the composite field is regulated by the intensity of the applied field to ensure that the composite field is always unipolar; that is, the composite field is always in the same direction along predetermined axis A.

As stated, it has been found that rather precise relationships of the flux density of the combined magnetic field to the frequency of the fluctuations are used in the present invention to provide therapeutic results. These ratios of frequency to composite flux density are found in accordance with the following equation:

$$f_c/B = q/(2\pi m)$$

where $f_c$ is the frequency of the combined magnetic field in Hertz, B is the net average value of the magnetic flux density of the combined magnetic field parallel to predetermined axis 50 in Tesla, q/m has a value of from about $5 \times 10^5$ to about $100 \times 10^6$ Coulombs per kilogram. B preferably has a value not in excess of about $5 \times 10^{-4}$ Tesla.

In another embodiment of the present invention, values for q and m are determined with reference to a preselected ionic species. It will be known by those skilled in the art that the biochemical milieu of a particular tissue comprises a mixture of various ions in the intercellular and interstitial fluid. These ions include potassium ions, magnesium ions, sodiums ions, chloride ions, phosphate ions, sulfate ions, carbonate ions, bicarbonate ions and the like and various ions formed by the dissociation of amino acids, proteins, sugars, nucleotides and enzymes. Applicants have found that by utilizing the values of charge and mass for a preselected ion in the equation set forth above, which will be recognized by those skilled in the art as the cyclotron resonance relationship solved for $f_c/B$, ratios of frequency to magnetic flux density can be determined which serve to regulate growth characteristics of living tissue in accordance with the present invention. By using the charge-to-mass ratio of a preselected ion, a specific cyclotron resonance frequency for the ion can be determined. By then tuning deformable tissue growth regulator 120 to maintain a combined magnetic flux density having the proper cyclotron resonance frequency, living tissue containing the preselected ion can be treated to being about changes in growth characteristics. Again, evidence indicates that the beneficial results of the present invention in this embodiment are achieved when the preselected ion absorbs energy from the magnetic field of the present invention having the desired parameters.

It will be appreciated by the prior explanation of preferred embodiment of the present invention and from the equation for establishing a cyclotron resonance relationship, that either the frequency of the fluctuating magnetic field or the magnitude or intensity of the magnetic flux density along the predetermined axis, or both the frequency and the intensity of the flux density, can be adjusted to provide a magnetic field within volume 168 which has the desired characteristics. However, as stated, it is preferred to maintain a constant frequency which thus requires that the intensity of the applied magnetic flux density be adjusted to compensate for changes in the local magnetic field in order to maintain a constant ratio of frequency to magnetic flux density. This is most preferably performed by the microcontroller in connection with both the field generating means and the field-sensing device. Alternatively, as stated, if changes in the combined magnetic flux density along the axis will occur due to changes in the orientation of deformable tissue growth regulator 120 with respect to the local magnetic field, the frequency of the oscillations can then be changed so that the preferred therapeutic ratio is maintained. Once again, it is important to realize that the value of B is the average composite magnetic flux density parallel to the predetermined axis since the magnitude of the flux density changes as the field is oscillated. It will be understood that detection of changes in the magnetic field due to changes in the ambient component should be at intervals frequent enough to provide a frequency-to-magnetic field ratio which is substantially constant, notwithstanding the changes in the local field component.

Referring now to FIG. 2 of the drawings, each field coil 142, 144 preferably has up to about 3000 turns or loops of conducting wire the diameter of each loop being preferably up to about 300 centimeters. The number of turns of wire n, the diameter of the coils, the separation of the coils, and the wire gauge are critical only insofar as conventional practice requires constraints on these and other design parameters to allow optimal performance characteristics in achieving predetermined flux densities as required in the preferred practice of the present invention. As stated, other magnetic field generating means may be suitable for use in the present invention and are contemplated as falling within the scope of this invention. In another embodiment, field coils 142 and 146 are simply coated with latex or the like by dipping the coils in a latex bath which produces a latex coating that allows the coils to be easily deformed to a desired shape.

It may also be appropriate in some instances to reduce components of the local magnetic field which are not parallel to predetermined axis A to zero through the use of additional coils positioned at right angles to deformable treatment pads 130, 132 to create an opposite but equal field, but this is not deemed necessary.

Referring now to FIG. 4 of the drawings, a block diagram is shown which depicts one preferred arrangement of the circuits of deformable treatment pads 120 in functional segments. Numerous other circuit arrangements may be possible if the principles of the present invention are faithfully observed. Microcontroller or microprocessor 200 is seen by which the composite magnetic field is maintained at a constant predetermined level despite changes in the ambient component as previously described. In this respect, input 202 is provided by which a set point value of the predetermined composite magnetic flux density along a predetermined axis through the target tissue is input into microprocessor 200. As will be shown, the composite field strength is compared to this set point value to generate an error equal to the difference in the set point value and the measured value of the composite magnetic flux density along the axis.

Magnetic field sensor 204 is provided by which the magnitude of the composite field which passes through the target tissue along the axis is measured. It is preferred that magnetic field sensor 204 comprise a Hall-effect device which, as will be known by those skilled in the art, produces an analog signal. The magnetic field sensor 204 constantly monitors the composite magnetic field, sending a signal to microprocessor 200. It will be understood that the output of a Hall-effect magnetic sensor is relatively small; thus, magnetic field sensor amplifier 206 is provided by which the signal from magnetic field sensor 204 is amplified, for example, up to three thousand times its original value. Since a Hall-effect device produces an analog signal, analog-to-digital converter 207 is provided by which the amplified signal from magnetic field sensor 204 is converted to a digital signal which can be used by microprocessor 200. It is preferred that the analog-to-digital converter be provided on-board the microprocessor chip.

As will be appreciated, the amplification of the magnetic field sensor signal may produce an unwanted noise level. Also, sudden changes in the magnetic field intensity may occur which make it difficult to determine the true average value of the composite magnetic flux density. Hence, the signal from analog-to-digital convertor 206 which is input into microprocessor 200 is filtered by software filter 208 to remove shot noise and sudden fluctuations in the composite field detected by magnetic field sensor 204. Although it is preferred that filter 208 comprise software in microprocessor 200, a discrete filter could be used. In this embodiment, software filter 208 is a digital filter, preferably an integrator with a time constant of approximately 0.5 seconds. In other words, the changes in the magnitude of the composite magnetic field which are compensated for by increasing or decreasing the applied field are long-term changes of 0.5 seconds or more which result primarily from changes in the orientation of regulator 120 with respect to the ambient field component. Hence, the time constant of filter 208 should be such that momentary fluctuations are filtered out.

Microprocessor 200 includes logic which calculates the non-zero net average value of the composite magnetic flux density. This non-zero average value is then compared at comparator 210 in microprocessor 200 to the predetermined dc reference or offset value which is input into microprocessor 200 via input 202. It should be noted that this reference value is preferably established by dedicated circuitry in microprocessor 200, although variable input means could be included by which the set point value could be changed. An error statement is then generated defining the difference in the measured value of the composite magnetic flux density and the set point or reference value. Microprocessor 200 then determines the magnitude of the output necessary to drive magnetic field generating coils 212 to bring the composite magnetic flux density back to the set point.

Software field modulator or oscillator 214 is provided by which an ac or fluctuating component is superimposed on the digital output signal which is input into digital-to-analog converter 216. From the previous discussion of the present invention, it will be understood that software field modulator 214 of microprocessor 200 in the preferred embodiment of the present invention is preset to a fixed, predetermined frequency to produce the desired predetermined, growth-regulating ratio of frequency-to-magnetic flux density value. In another embodiment, the feedback system of the present invention is such that changes in the composite magnetic flux density are measured, whereupon microprocessor 200 determines the necessary change in frequency to maintain the predetermined relationship. In that embodiment, software field modulator 214 produces the requisite ac frequency. It is again preferred that digital-to-analog converter 216 be provided on-board the microprocessor chip. Hence, software field modulator 214 provides the ac component at node 218.

The signal from digital-to-analog converter 216 is fed to voltage-to-current amplifier 220, the output of which drives magnetic field generating coils 212 in the desired manner. Hence, the composite field is held substantially constant despite changes in the ambient component.

While several arrangements of power sources are suitable, it is preferred that power supply 222 be provided to power magnetic field sensor amplifier 206, microprocessor 200 and magnetic field sensor 204, the latter via bias circuitry 224. A separate power source 226 is preferred for voltage to current amplifier 220.

The present invention further includes a method of controlling the growth of living tissue which encompasses the use and operation of the apparatus of the present invention as described more fully in the aforementioned U.S. patent application Ser. No. 172,268.

While a particular embodiment of this invention is shown and described herein, it will be understood, of course, that the invention is not to be limited thereto since many modifications may be made, particularly by those skilled in this art, in light of this disclosure. It is contemplated therefore by the appended claims to cover any such modifications that fall within the true spirit and scope of this invention.

What is claimed is:

1. An apparatus for the regulation of in vivo tissue development, comprising:
   a pair of deformable field coils for generating an applied magnetic flux in a predetermined space and parallel to a predetermined axis which projects through said predetermined space, said predetermined space being occupied by a portion of living tissue of a subject;
   a field-sensing device for measuring both AC and DC magnetic flux density parallel to said predetermined axis in said predetermined space;
   microprocessing means including means for oscillating said applied magnetic flux in communication with said field coils and said field-sensing device for creating and maintaining a predetermined relationship between the frequency of said magnetic flux and the intensity of said magnetic flux density to provide a fluctuating magnetic field which regulates the development of said living tissue; and
   each of said field coils being enclosed in separate housings of deformable non-magnetic material, and said housings being shaped to correspond to the individual shape of the subject.

2. The apparatus for the regulation of in vivo tissue development recited in claim 1, wherein said field coils are arranged in generally Helmholtz configuration with respect to said predetermined space.

3. The apparatus for the regulation of in vivo tissue development recited in claim 1, wherein said field-sensing device is a Hall-effect device.

4. The apparatus for the regulation of in vivo tissue development recited in claim 1, further including means attached to said first and second housings for securing said apparatus into position relative to said predetermined space.

5. The apparatus for the regulation of in vivo tissue development recited in claim 1, wherein said magnetic flux is combined with an ambient magnetic flux present in said region of tissue to create a composite magnetic flux density.

6. An apparatus as recited in claim 1, wherein said field-sensing device is enclosed in one of said housings.

7. An apparatus as recited in claim 6, wherein said microprocessor means also is enclosed in one of said housings.

8. A method for regulating the growth characteristics of tissue in vivo, comprising the steps of:
   shaping a magnetic field generating means, that comprises deformable field coils mounted in housings of deformable non-magnetic material, to an area to be treated;
   positioning the magnetic field generating means adjacent to a living subject such that a region of tissue of said subject occupies a predetermined space;
   generating a magnetic flux with said magnetic field generating means, said magnetic flux extending through said region of tissue and parallel to a predetermined axis projecting through said predetermined space;
   measuring the total magnetic flux density parallel to said predetermined axis with a field-sensing device; and
   fluctuating said generated magnetic flux and controlling the density of said generated magnetic flux, in response to said measured magnetic flux, to create and maintain a predetermined relationship between the frequency of said fluctuations and the magnitude of said magnetic flux density which regulates development of said tissue.

9. The method for regulating the growth characteristics of tissue in vivo recited in claim 8, wherein said magnetic flux is combined with an ambient magnetic flux present in said region of tissue to create a composite magnetic flux density.

10. The method for regulating the growth characteristics of tissue in vivo recited in claim 8, wherein the field-sensing device is mounted in one of said housings.

* * * * *